United States Patent
Lewis et al.

(10) Patent No.: US 7,273,517 B1
(45) Date of Patent: Sep. 25, 2007

(54) NON-PLANAR MICROFABRICATED GAS CHROMATOGRAPHY COLUMN

(75) Inventors: Patrick R. Lewis, Albuquerque, NM (US); David R. Wheeler, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 331 days.

(21) Appl. No.: 11/067,107

(22) Filed: Feb. 25, 2005

(51) Int. Cl.
*B01D 53/02* (2006.01)

(52) U.S. Cl. ............... 96/101; 95/82; 95/86; 95/87; 73/23.39

(58) Field of Classification Search ............ 96/101, 96/104–107; 95/82–87; 73/23.35, 23.36, 73/23.37, 23.39, 23.4, 23.42; 422/89; 210/198.2, 210/656
See application file for complete search history.

(56) References Cited

U.S. PATENT DOCUMENTS

| | | | | |
|---|---|---|---|---|
| 3,149,941 A * | 9/1964 | Barnitz et al. | ............... | 96/101 |
| 3,449,938 A * | 6/1969 | Giddings | ............... | 73/23.39 |
| 3,503,712 A * | 3/1970 | Sussman | ............... | 422/191 |
| 4,935,040 A * | 6/1990 | Goedert | ............... | 73/23.22 |
| 5,132,012 A * | 7/1992 | Miura et al. | ............... | 210/198.2 |
| 5,376,252 A * | 12/1994 | Ekstrom et al. | ............... | 204/603 |
| 5,792,943 A * | 8/1998 | Craig | ............... | 73/61.52 |
| 6,068,684 A | 5/2000 | Overton | | |
| 6,068,780 A * | 5/2000 | Yu | ............... | 216/10 |
| 6,296,685 B1 * | 10/2001 | Cammann et al. | ............... | 95/45 |
| 6,332,568 B1 | 12/2001 | Christenson | | |
| 6,454,840 B1 * | 9/2002 | Gellert et al. | ............... | 96/101 |
| 6,527,890 B1 * | 3/2003 | Briscoe et al. | ............... | 156/89.11 |
| 6,568,244 B2 * | 5/2003 | Binz et al. | ............... | 73/23.2 |
| 6,607,580 B1 * | 8/2003 | Hastings et al. | ............... | 95/87 |
| 6,663,697 B1 | 12/2003 | Kottenstette et al. | | |
| 6,666,907 B1 | 12/2003 | Manginell et al. | | |
| 6,670,024 B1 * | 12/2003 | Yu | ............... | 428/209 |
| 6,699,392 B1 * | 3/2004 | Manginell et al. | ............... | 210/656 |
| 6,706,091 B1 | 3/2004 | Robinson et al. | | |
| 6,732,567 B2 * | 5/2004 | Briscoe et al. | ............... | 73/23.39 |

(Continued)

OTHER PUBLICATIONS

Greg Frye-Mason, Hand-Held Miniature Chemical Analysis System (μChemLab) for Detection of Trace Concentrations of Gas Phase Analytes, Presented at Fourth Int. Conf. On Micro Total Analysis Systems, Enslcade, Netherlands on May 14-18, 2000.

(Continued)

*Primary Examiner*—Duane Smith
*Assistant Examiner*—Robert A Clemente
(74) *Attorney, Agent, or Firm*—Kevin W. Bieg

(57) ABSTRACT

A non-planar microfabricated gas chromatography column comprises a planar substrate having a plurality of through holes, a top lid and a bottom lid bonded to opposite surfaces of the planar substrate, and inlet and outlet ports for injection of a sample gas and elution of separated analytes. A plurality of such planar substrates can be aligned and stacked to provide a longer column length having a small footprint. Furthermore, two or more separate channels can enable multi-channel or multi-dimensional gas chromatography. The through holes preferably have a circular cross section and can be coated with a stationary phase material or packed with a porous packing material. Importantly, uniform stationary phase coatings can be obtained and band broadening can be minimized with the circular channels. A heating or cooling element can be disposed on at least one of the lids to enable temperature programming of the column.

19 Claims, 5 Drawing Sheets

U.S. PATENT DOCUMENTS

| | | | |
|---|---|---|---|
| 6,838,640 B2* | 1/2005 | Wise et al. | 219/209 |
| 7,147,695 B2* | 12/2006 | Mitra | 96/101 |
| 7,157,004 B1* | 1/2007 | Sylwester | 210/656 |
| 2003/0118481 A1* | 6/2003 | Briscoe et al. | 422/89 |
| 2003/0145725 A1* | 8/2003 | Hastings et al. | 95/87 |
| 2003/0233862 A1* | 12/2003 | Wise et al. | 73/23.39 |
| 2004/0255643 A1* | 12/2004 | Wise et al. | 73/23.39 |
| 2005/0223775 A1* | 10/2005 | Klee et al. | 73/23.41 |
| 2006/0144237 A1* | 7/2006 | Liang et al. | 96/101 |

OTHER PUBLICATIONS

C. M. Matzke, Microfabricated silicon gas chromatographic microchennels: fabrication and performance, Proceedings of SPIE, Micromachining and Microfabrication Process Technology IV, 3511, 262 (1998).

Gordon Lambertus, Design, Fabrication, and Evaluation of Microfabricated Columns for Gas Chromatography, Anal. Chem., 2004, 76, 2629-2637.

Glen E. Spangler, Height Equivalent to a Theoretical Plate Theory for Rectangular GC Columns, Anal. Chem. 1998, 70, 4805-4816.

Glen E. Spangler, Relationships for Modeling the Performance of Rectangular Gas Chromatographic Columns, J. Microcolumn Separations, 13, 7, 285-292, 2001.

Marieke Van Deursen, Theoretical Design Considerations for Multicapillary Columns in Fast Gas Chromatography, J. High Resol. Chromatogr., 1999, 22, 2, 119-122.

Mark Van Lieshout, A Practical Comparison of Two Recent Strategies for Fast Gas Chromatography: Packed Capillary Columns and Multicapillary Columns, J. Microcolumn Separations, 11, 2, 155-162, 1999.

* cited by examiner

NON-PLANAR MICROFABRICATED GAS CHROMATOGRAPHY COLUMN

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to microanalytical systems and, more particularly, to a non-planar microfabricated gas chromatography column that can be used to separate chemical analytes in a gas sample mixture.

BACKGROUND OF THE INVENTION

Gas chromatography (GC) relies upon the chemical equilibria of analytes between a mobile phase and a stationary phase in a GC column to bring about a temporal separation of the analytes in a gas mixture into a series of elution bands. Most current methods of gas chromatography rely on an open capillary tube with a stationary phase coating the inner wall of the tube to generate chemical separations. In addition, GC columns that are packed with a support that can be coated with a stationary phase can achieve chemical separations. However, eddy diffusion and channeling, due to the presence of particles, can lead to band broadening and poorer detection limits in packed columns. Therefore, open capillary columns generally offer improved separations with higher resolution, reduced time of analysis, and improved column efficiency as compared to packed columns. Furthermore, because of their open geometry and lower flow resistance, a capillary tube has a lower pressure drop, enabling longer columns to be used. For conventional bench top methods of gas chromatography, these columns are very long, usually 30 to 60 meters for open capillary tubes, as compared to as short as 2 meters for packed columns. However, narrow-bore capillary columns have a low sample capacity and working range, due to the low volume of stationary phase present in the column. In addition, injection and detection must be fast enough to take advantage of the reduced band broadening obtainable with a fast capillary column. A compromise solution to obtain fast separations with acceptable sample capacity is the multi-capillary column, comprising a bundle of narrow-bore capillary tubes running in parallel. Fast separations are achievable because narrow-bore capillaries are used, while the dynamic range can be high. However, each capillary of the multi-capillary column must have the same diameter, length, and thickness of stationary phase coating to prevent band broadening and loss of efficiency. In practice, the optimum column type and column operating parameters depend on a number of factors, including the complexity of the sample mixture, resolution required, analysis time and sample capacity desired, and pressure drop acceptable.

Portable, handheld microanalytical systems, which have been termed "chemical laboratories on a chip," are being developed based on gas chromatography to enable the rapid and sensitive detection of particular chemicals, including pollutants, high explosives, and chemical and biological warfare agents. In particular, on-site monitoring with a portable system results in much shorter analysis turn-around times and can reduce the risk of contamination, sample loss, and sample decomposition during transport. These microanalytical systems should provide a high chemical selectivity, to discriminate against potential background interferents, and the ability to perform the chemical analysis on a short time scale. In addition, these systems should be small, lightweight, and require low maintenance and low electrical power consumption as are needed for prolonged field use. However, to achieve these objectives, resolution and sensitivity are often compromised. See, e.g., Frye-Mason et al., "Hand-Held Miniature Chemical Analysis System (μChemLab) for Detection of Trace Concentrations of Gas Phase Analytes," *Micro Total Analysis Systems* 2000, 229 (2000).

Both open and packed in-chip channels have been used with current GC-based microanalytical systems. In particular, etched silicon channels are commonly used for microfabricated GC columns. Anisotropic wet etching or reactive ion etching can be used to form high-aspect-ratio rectangular channels with precisely controlled channel depth and width in a substrate. Typically, rectangular channels are about 10 to 80 microns wide and about 200 to 400 microns deep etched in the surface of a silicon wafer. For dense packing, the channels typically have a spiral or serpentine pattern in a die that is approximately one square centimeter in area. After etching, a glass coverplate is bonded to the etched silicon surface. The inside surfaces of the channel can be coated with a stationary phase material to enhance the separation of the chemical analytes of interest in the gas sample. For example, the stationary phase material can be a polymer having a specific chemical group with the proper physico-chemical interaction to cause separation of the analytes. Instead of using a stationary phase material to coat the surfaces of the channel, the channel can alternatively be filled with a porous packing material. Finally, the microfabricated column can be heated by a thin-film resistance heater deposited on the unetched side of the substrate. Overall column length is typically about 1 meter for open channels and as short as 10 centimeters for packed channels. See C. M. Matzke et al., "Microfabricated Silicon Gas Chromatographic MicroChannels: Fabrication and Performance," *Proceedings of SPIE, Micromachining and Microfabrication Process Technology IV,* 3511, 262 (1998); G. Lambertus et al., "Design, Fabrication, and Evaluation of Microfabricated Columns for Gas Chromatography," *Anal. Chem.* 76, 2629 (2004); U.S. Pat. No. 6,068,684 to Overton; and U.S. Pat. No. 6,663,697 to Kottenstette et al., which are incorporated herein by reference.

Such high-aspect-ratio rectangular channels can provide relatively high column efficiency combined with relatively high volumetric flow rates and high stationary phase surface area. This is because, with a rectangular column, resolution is primarily controlled by the channel width and volumetric flow is determined by the channel cross section. However, because of diffusion along the height dimension of the rectangular channel, high-aspect-ratio rectangular columns can suffer from band broadening. Furthermore, the rectangular geometry is difficult to coat with a satisfactorily uniform stationary phase and is sensitive to defects in the channel height that reduce the overall separation efficiency. This coating difficulty results in buildup of the stationary phase in the corners of the rectangular channel. Finally, long column lengths are required for the separation of many analytes. Simply making longer spiral or serpentine planar columns leads to large die sizes, which are not easily integrated with a microfabricated inlet system or detector of a microanalytical system.

Therefore, a need remains for a microfabricated GC column that minimizes band broadening, enables long column lengths with low pressure drop, enables uniform stationary phase coatings, and provides a column configuration that can be easily integrated with other microfabricated components to provide a compact and fast microanalytical system.

SUMMARY OF THE INVENTION

The present invention is directed to a non-planar microfabricated GC column for separation of analytes in a sample gas mixture, comprising a planar substrate having a plurality of through holes; a top lid and a bottom lid bonded to opposite surfaces of the planar substrate, each lid having a plurality of vias to interconnect the plurality of through holes to provide at least one continuous flow channel; at least one inlet port in the top or bottom lid for injection of the sample gas mixture; and at least one outlet port in the top or bottom lid for elution of the separated analytes. The vias can interconnect the through holes in series, series-parallel, or parallel column configurations. The column can further comprise additional planar substrates that are stacked with their through holes aligned to provide for a longer continuous flow channel or a longer multi-capillary column. The through holes preferably have a circular cross section and can be coated with a stationary phase or packed with a porous packing material. Finally, the vias can interconnect the through holes in a configuration to provide at least two separate channels for multi-channel or multi-dimensional gas chromatography. A heating or cooling element can be disposed on at least one of the lids to enable temperature programming of the column.

The non-planar microfabricated GC column has several advantages compared to prior planar microfabricated GC columns having high-aspect-ratio rectangular channels. Very long non-planar columns can be made having the same arial footprint as much shorter columns. Importantly, uniform stationary phase coatings can be obtained and band broadening can be minimized with the circular channels enabled by the non-planar GC column microfabrication processes. Finally, the versatility of microfabrication techniques enables the integration of the non-planar GC column with other components, such as pumps, valves, inlet systems, preconcentrators, and detectors, in a microanalytical system.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

FIG. 2A shows a series configuration comprising an array of through holes in a substrate serially interconnected by semicircular vias formed in top and bottom lids. FIG. 2B shows a series-parallel column configuration. FIG. 2C shows a column configuration that enables dual-channel or two-dimensional chromatography.

DETAILED DESCRIPTION OF THE INVENTION

Figure 1:
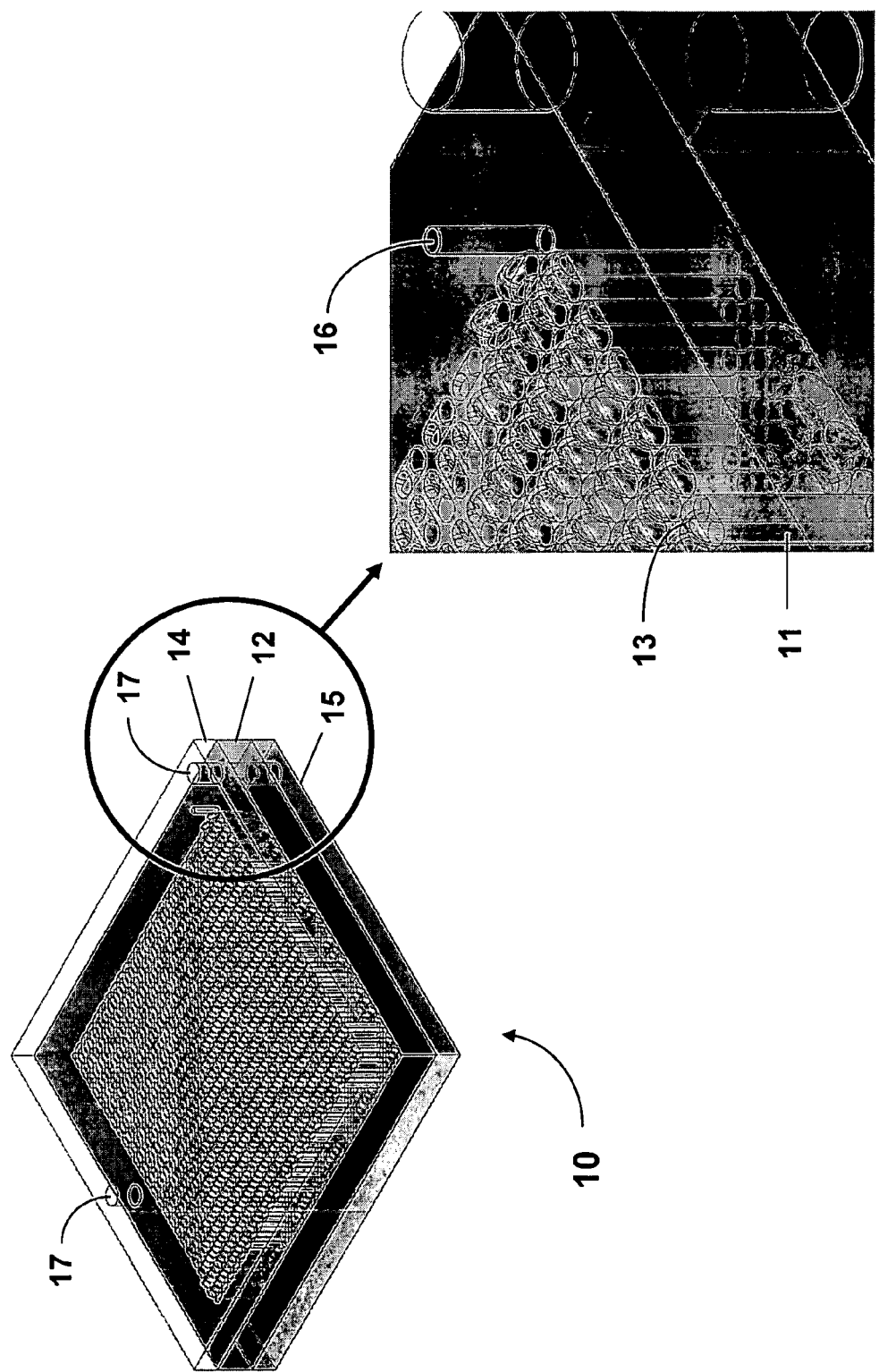
FIG. 1 shows a schematic illustration of an exemplary non-planar microfabricated GC column.

In FIG. 1 is shown a schematic illustration of an exemplary non-planar microfabricated GC column 10 of the present invention. The column 10 comprises a parallel array of holes 11 etched through a planar substrate 12. The sidewalls of the holes 11 can be coated with a stationary phase, or the holes can be filled with a porous packing material. The ends of adjacent holes 11 can be interconnected in a serial arrangement by rectangular or semicircular vias 13 (e.g., 180° elbows or half-annuli) formed in a top lid 14 and a bottom lid 15. As shown, the interconnected holes can form a continuous serpentine flow channel, much like a shell and tube heat exchanger. An inlet port 16, for injection of a sample gas mixture, and an outlet port (not shown), for elution of the separated analytes, can be formed through the lids 14 and 15. The substrate 12 and top and bottom lids 14 and 15 can be aligned by means of alignment pins 17 and bonded together to form a leak-tight seal.

Figure 2A:
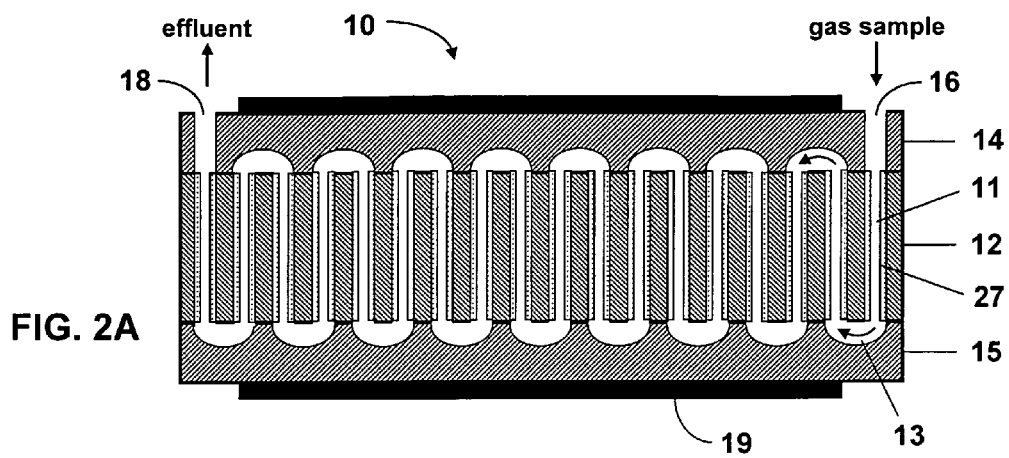
FIGS. 2A-2C show cross-sectional side views of different channel configurations can also be used to provide the non-planar microfabricated GC column.

FIG. 2A shows a cross-sectional side view of the exemplary column 10 illustrated in FIG. 1. The column 10 can be fabricated using techniques and materials generally known to the integrated circuit (IC) manufacturing and microelectromechanical systems (MEMS) industries. See Mohamed Gad-el-Hak, *The MEMS Handbook*, CRC Press (2002). For example, the planar substrate 12 can comprise a single crystal silicon wafer. An N×N array of holes 11 can be etched through the silicon wafer. Using a patterned photoresist to define the hole pattern, holes with nearly vertical channel sidewalls can be obtained using a Bosch plasma etching process, as described by Matzke et al. Preferably, a square array of open cylindrical holes is etched through the thickness of wafer, perpendicular to the surface of the substrate 12. The silicon channel sidewalls can be thermally oxidized to produce a silica surface similar to that of fused silica capillary tubing. The top and bottom lids 14 and 15 can be Pyrex, although other materials that can be easily bonded to the substrate material can also be used. Rectangular or semicircular vias 13 can be formed in top and bottom lids 14 and 15 by machining, or wet chemical or plasma etching. Through holes can be provided in one or both lids for the inlet and outlet ports 16 and 18. The lids 14 and 15 can be aligned to the channels 11 by placing the vias 13 over the channel ends so as to connect adjacent channels. Keying of the substrate 12 and lids 14 and 15 with alignment pins facilitates the assembly, and avoids misdirecting, misaligning, or plugging of the gas flow. Pyrex lids can then be anodically or fusion bonded to the oxidized surfaces of the silicon substrate to provide a hermetic and leak-tight seal. Since gas chromatography usually requires heat, a heating element 19 can be disposed on one or both of the lids 14 and 15. For example, resistive heater element can be patterned on the outer surface of the top and/or bottom lid. Alternatively, a thermoelectric cooler can be disposed on one or both of the lids to enable heating from sub-ambient temperatures. By controlling the electrical power to the heating element 19, the column temperature can be programmed to reduce analysis time and improve overall detectability of the analytes. See U.S. Pat. No. 6,666,907 to Manginell et al. and U.S. Pat. No. 6,706,091 to Robinson et al., which are incorporated herein by reference.

Alternatively, the GC column 10 can be fabricated using a LIGA process (LIGA is the German acronym for Lithographie, Galvanoformung, and Abformung). High-aspect-ratio though holes can be easily formed in a wide variety of substrate materials using the LIGA-based techniques. The substrate 12 can comprise glass, graphite, ceramic, plastic, metal, alloy, or other suitable GC column material. A typical LIGA-based microfabrication process comprises exposing a photoresist to a collimated beam of high energy x-rays through a patterning mask, developing the photoresist to provide a mold, filling the voids of the mold with a structural material, planarizing the exposed surface of the electrodeposit, and removing the mold to yield the desired microstructure. Typical deep x-ray lithography-produced microstructures can be fabricated with nearly arbitrary in-plane geometry, aspect ratios of 100 or greater, feature heights of up to about one millimeter or greater, and sidewall surface roughness of about 10 nm RMS. For example, to form an array of holes in a substrate, a thick layer of positive photoresist (e.g., PMMA) can be exposed to the x-ray beam through a patterning mask comprising an array of x-ray absorbing dots. The exposed areas of the photoresist can then be developed to provide a mold comprising an array of posts. If the mold is to be filled by electroforming, the photoresist mold can first be coated with a plating base. A structural material can then be electroformed on the plating base to fill the mold. Typical electroplated materials include copper and nickel. The rough, electroplated free surface of the filled mold can then be planarized by diamond lapping or the like. The remaining resist mold material can then be dissolved away to provide an array of through holes 11 in the electroformed substrate 12. Alternatively, an intermediate mold comprising an array of posts of the electroplated material can be formed from a photoresist mold comprising an array of holes. Other substrate materials can then be used to fill the intermediate mold via hot embossing, injection molding, glass or ceramic casting, etc. Similarly, top and bottom lids 14 and 15 with rectangular or semicircular vias 13 can be formed using LIGA processes.

The vias 13 in the lids 14 and 15 can then be aligned to the through holes in the LIGA substrate 12 and the assembly can be bonded together. For example, a wafer-scale assembly method comprising precision aligned layer-to-layer diffusion bonding that can be used to bond the LIGA substrate 12 and lids 14 and 15 together is described in U.S. Pat. No. 6,332,568 to Christenson, which is incorporated herein by reference. This layer-to-layer method can be repeated as many times a needed to build up a multi-layer stack comprising a plurality of through-hole LIGA substrates. Precision alignment tolerances of below one micron have been achieved with this method.

Using either MEMS or LIGA fabrication processes, the through holes 11 can have a variety of hole patterns and cross sections. For example, the hole pattern can comprise a 50×50 square array of 100-micron-diameter through holes that are spaced about 50 microns apart in a 500-micron-thickness substrate. The interconnected holes form a 1.25-meter-long, serpentine continuous flow channel that occupies an area of about 1 cm$^2$. Additional through-hole substrates can be aligned and stacked to provide an even longer column having the same footprint as a shorter column. For example, 20 through-hole substrates can be stacked to form a continuous flow channel that is about 25 meters long and fits in a volume of about 1 cm$^3$. As will be readily apparent to those skilled in the art, various substrate and lid materials, substrate and stack thicknesses, hole patterns, and hole geometries can also be used.

The holes 11 preferably have a circular cross section, although other cross sections can also be used. A channel having a circular cross section will minimize band broadening. For example, it has been found that a circular column of large diameter (e.g., 250 µm) will provide the same number of theoretical plates as a rectangular column of similar length having a much smaller width dimension (e.g., 100 µm). Furthermore, a circular cross section enables uniform stationary phase deposition by minimizing the length of sharp corners where stationary phase material can build up.

The inside surfaces of the holes 11 can be coated with a stationary phase material 27 to facilitate the separation of the analytes in the gas sample. A typical stationary phase comprises a polymer synthesized with specific chemical groups having the proper physico-chemical interactions to cause the separation of the gas analytes of interest. For example, a nonpolar stationary phase can be used to separate analytes in relation to their boiling points. Alternatively, a polar stationary phase can be used to preferentially retain polar analytes. See R. L. Grob and E. F. Barry, *Modern Practice of Gas Chromatography*, Wiley-Interscience (2004).

The holes 11 can be coated with the stationary phase material by pushing a plug of the material through the holes or by filling the holes with a solvent containing the stationary phase material and then applying a vacuum to the end of the holes to dry the solvent out of the holes. The stationary phase can also be applied by gas or liquid phase deposition into the holes prior to bonding the lids to the substrate. Alternatively, solutions of polymeric stationary phases, or slurries of the stationary phase, can be dispersed in solvents that lend themselves to removal by vacuum sublimation. The solution can then be deposited in the holes and vacuum sublimation can be used to remove the solvent. Instead of using a stationary phase material to coat the surfaces of the holes, the holes can alternatively be filled with a porous packing material to make a packed column.

The circular channel geometry of the non-planar GC column enables more uniform stationary phase deposition and, consequently, less band broadening due to thickness variations, as can occur with rectangular channels. However, to avoid band broadening due to the interconnecting hairpin turns in the vias 13 in the top and bottom lids 14 and 15, it may be preferable to coat the through holes with the stationary phase prior to assembly and leave the semicircular vias 13 uncoated. After the through holes 11 are coated with stationary phase material, the substrate 12, top lid 14, and bottom lid 15 can then be bonded together.

Figure 3:
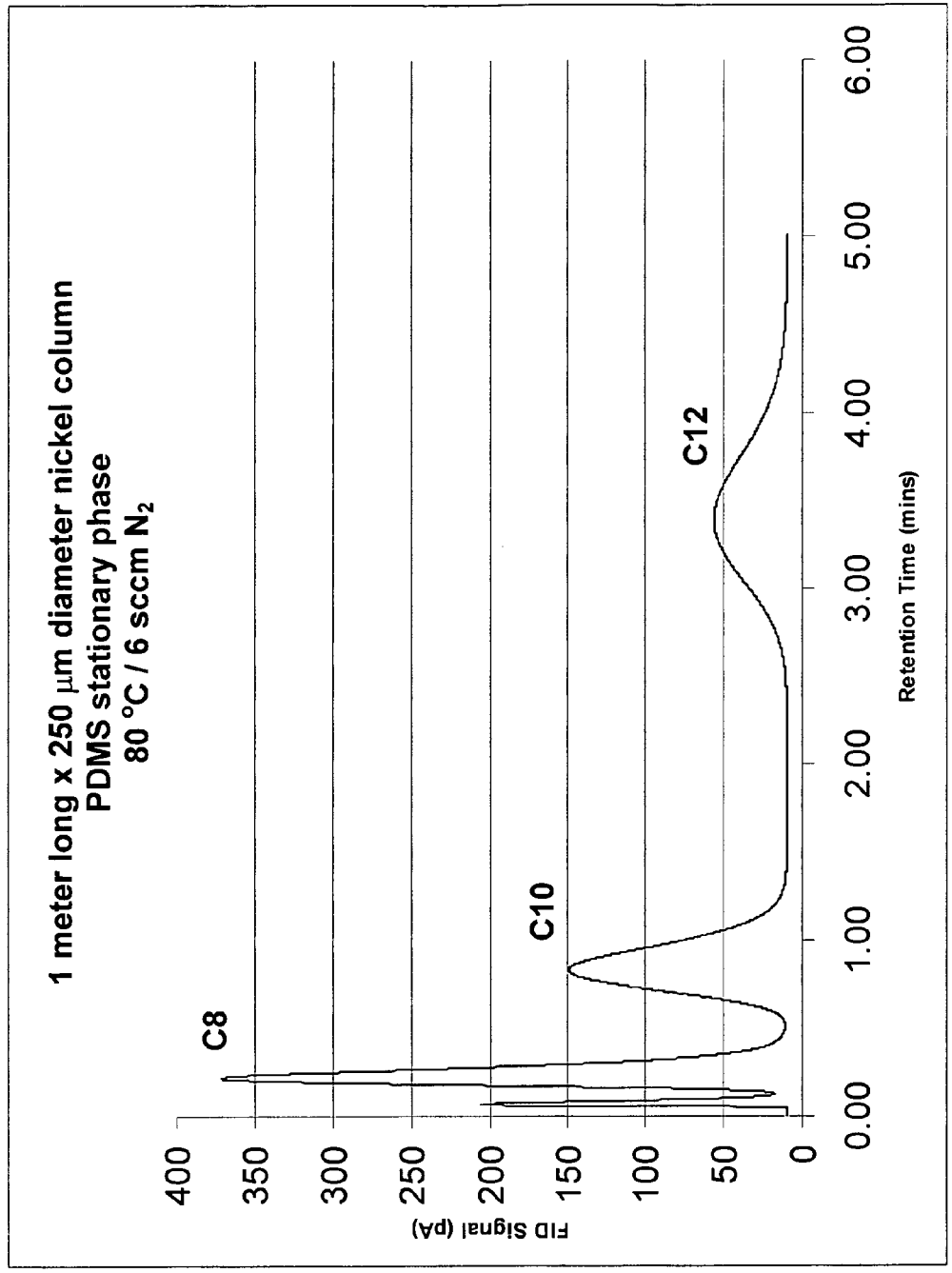
FIG. 3 shows a chromatogram of a sample gas mixture of non-polar analytes comprising C8 to C12 hydrocarbons, obtained using an isothermal non-planar microfabricated GC column of the type shown in FIG. 2A.

In FIG. 3 is shown a chromatogram of a nonpolar mixture of C8, C10, and C12 hydrocarbons obtained using an isothermal non-planar microfabricated GC column of the type shown in FIG. 2A. The GC column was formed using a LIGA process in a nickel substrate. The hole diameter was 250 microns and the serpentine continuous flow channel had a length of about one meter. The channel was coated with polydimethylsiloxane (PDMS) stationary phase material. The separated analytes were detected with a convention flame ionization detector (FID). The column temperature was kept at 80° C. The pressure drop across the column was 5 psi with a nitrogen carrier gas flow of 6 sccm. The chromatogram shows well-separated Gaussian peak shapes for the nonpolar hydrocarbons. Also, excellent retention is apparent from the baseline separation between the analytes.

Figure 4:
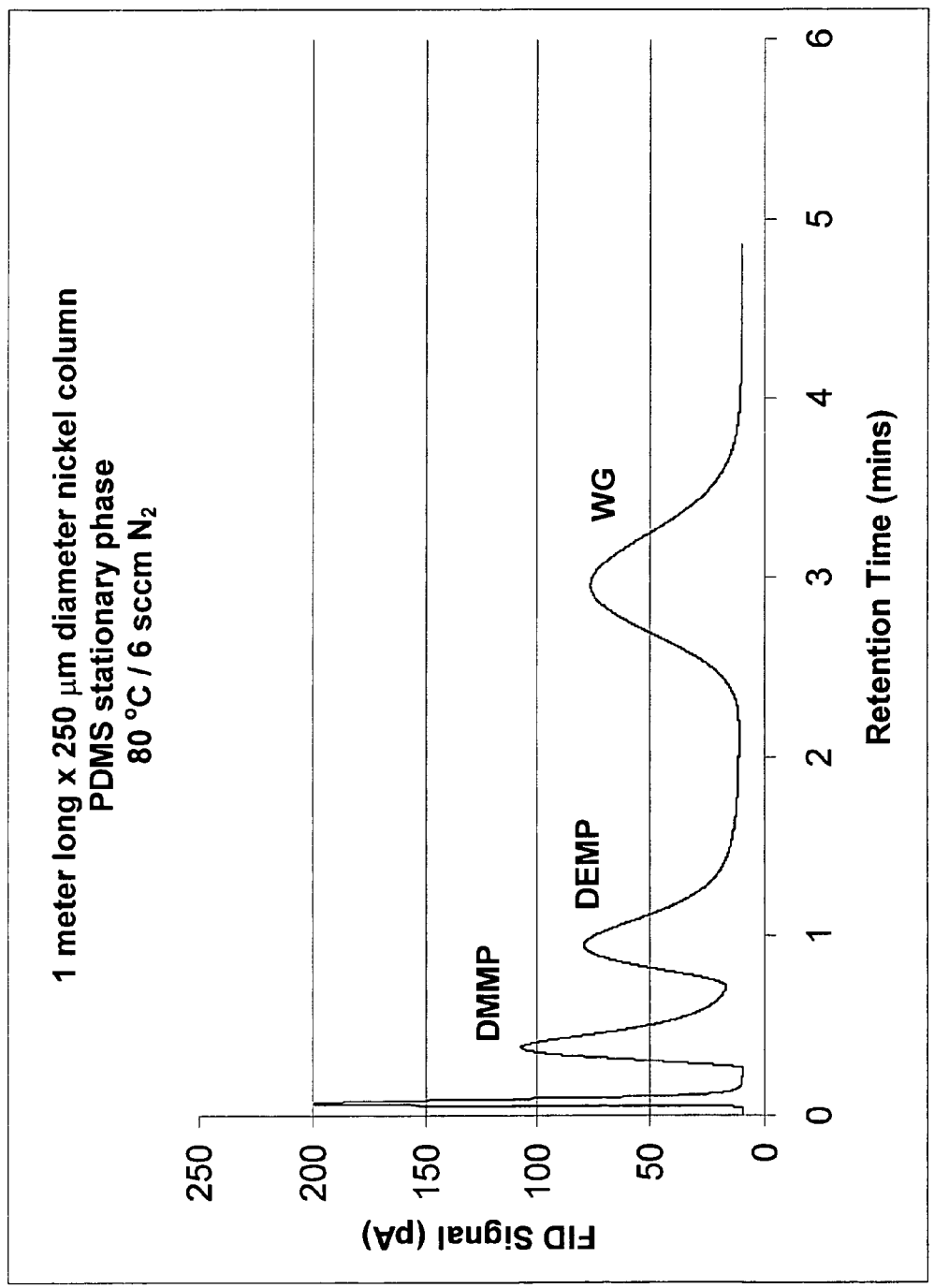
FIG. 4 shows a chromatogram of a sample gas mixture of polar analytes comprising dimethyl methyl phosphonate, diethyl methyl phosphonate, and wintergreen, obtained using an isothermal non-planar microfabricated GC column of the type shown in FIG. 2A.

In FIG. 4 is shown a chromatogram of a mixture of polar analytes, dimethyl methyl phosphonate (DMMP), diethyl methyl phosphonate (DEMP), and wintergreen (WG), obtained using the same isothermal column and carrier gas flow rate. Again, Gaussian peak shapes were obtained for the very polar DMMP and DEMP analytes, indicating through coverage of the channel sidewalls with the stationary phase. Good resolution is indicated by the baseline separation of the analytes.

Figure 2B:
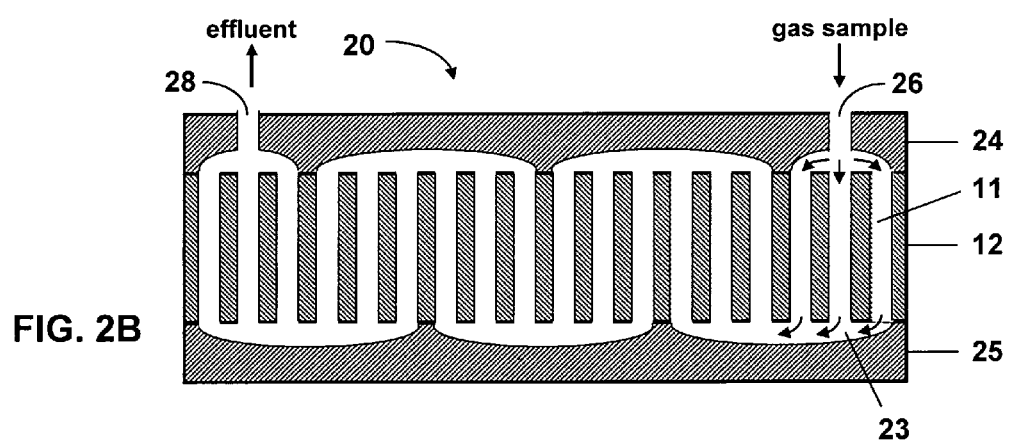

Alternative channel configurations can also be used to provide the non-planar microfabricated GC column of the present invention. For example, in FIG. 2B is shown a series-parallel column configuration 20, in which the gas sample entering in an inlet port 26 in a top lid 24 is split into a group of two or more parallel holes 11. The gas flow exiting from the group of holes 11 is discharged into a plenum 23 in the bottom 25 lid and redirected to another group of parallel holes. The gas flows through a series of groups of parallel holes and is eventually gathered and leaves the column through an outlet port 28. The sidewalls of the holes can be coated with a stationary phase material, or the holes can be packed with a porous packing material (not shown). A resistive heater element (not shown) can be patterned on the outer surface of the top and/or bottom lid to heat the column 20.

Figure 2C:
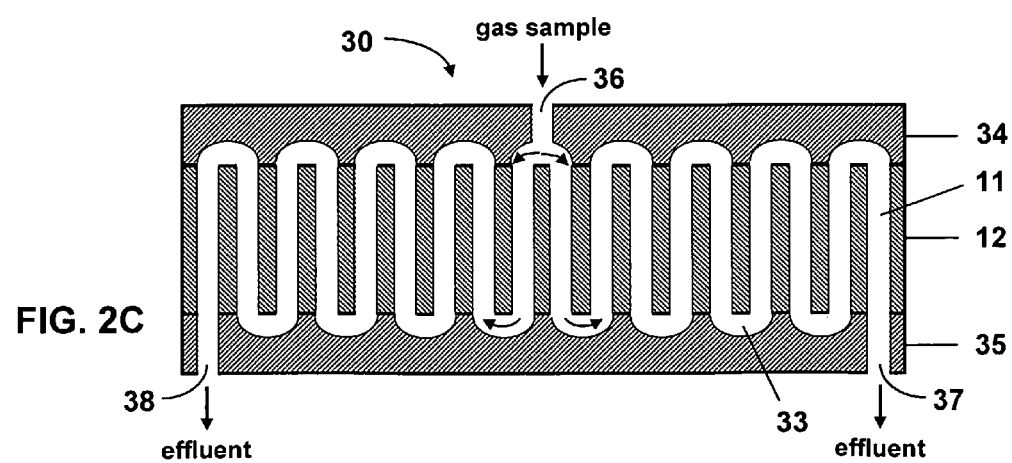

A common practice in analytical chemistry is dual-channel chromatography. In this procedure, columns of differing stationary phases are used to provide different retention times for the same analyte, or to simultaneously analyze different analytes. In FIG. 2C is shown a column configuration 30 that enables dual-channel chromatography. Flow of the sample gas into a port 36 is split into two separate channels, each channel comprising a series of holes 11 in the substrate 12 that are interconnected by vias 33 in the top and bottom lids 34 and 35 to provide a continuous serpentine flow channel. Ports 37 and 38 are provided for exit of the separated effluent from each channel. The channels can be independently coated with different stationary phase materials, or packed with different porous packing materials (not shown). A resistive heater element (not shown) can be patterned on the outer surface of the top and/or bottom lid to heat the column 30. Since both channels are in the same substrate 12, they can share the same heater, thus saving power.

The non-planar GC columns can be alternatively configured to enable multidimensional gas chromatography to improve the sensitivity, separation, and selectivity of trace analytes in complex mixtures. For example, using a GC×GC technique, a large quantity of sample can be injected into a first column and a small fraction of the separated effluent, containing the trace analyte, can be diverted to a second column for further separation. Therefore, the effluent exiting the second column is much purer than the effluent exiting the first column. The columns can have dissimilar stationary phases based on different retention mechanisms to optimize the effectiveness for separating the complex mixture. The two or more columns can be formed on the same substrate, or on separate substrates that are connected in series.

For example, two-dimensional gas chromatography can be achieved on the same substrate using the column configuration shown in FIG. 2C. A sample gas can be injected into the port 37. A portion of the temporally separated effluent from the first part of the column can be sent to a detector, another column, or simply vented at intermediate port 36 using appropriate valving. The remaining portion of separated effluent, containing the trace analyte, can be diverted to the second portion of the column and further separated in the second part of the column, exiting at port 38.

Figure 5:
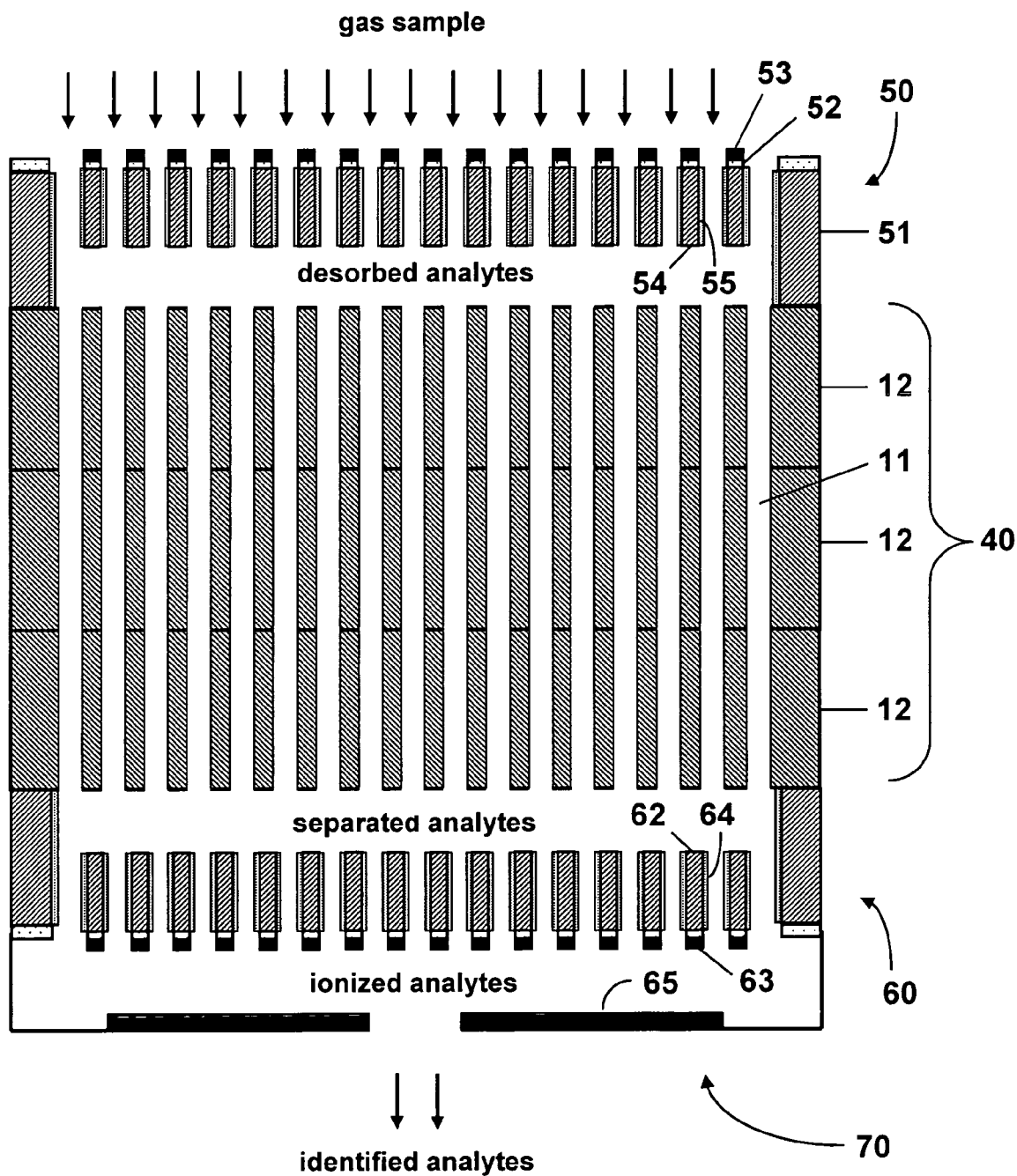
FIG. 5 shows a cross-sectional side view of a compact and fast microanalytical system comprising a microfabricated chemical preconcentrator, the non-planar microfabricated GC column, and a microfabricated thermionic detector.

The non-planar microfabricated GC column of the present invention can be integrated with a variety of microfabricated inlet systems and detectors, or can be used with conventional column inlet systems and detectors. As shown in FIG. 5, the non-planar GC column 40 can be integrated with a microfabricated chemical preconcentrator 50 and a microfabricated detector 60 to provide a compact and fast GC-based microanalytical system 70. This system 70 enables fast injection of desorbed analytes from the preconcentrator 50 and fast detection of the separated analytes by the detector 60 with very little dead volume between the sample collection, separation, and detection stages.

To prevent adverse broadening of peaks, the column inlet system must efficiently inject the sample into the column with a very narrow pulse width. The rapid desorption of an absorbed sample from a microfabricated chemical preconcentrator 50 can provide an extremely high quality injection for the gas chromatography separation stage. In particular, a non-planar chemical preconcentrator of the type disclosed in U.S. patent application Ser. No. 10/696,649 to Manginell et al. can be easily integrated with the non-planar GC column 40 of the present invention. The non-planar chemical preconcentrator has a high thermal efficiency and a low heat capacity, enabling rapid desorption of the sorbed chemical analyte with low power consumption. The non-planar chemical preconcentrator uses a high-surface area, low mass, three-dimensional, flow-through support structure that can be coated or packed with a sorptive material. As shown in FIG. 5, the non-planar chemical preconcentrator comprises a substrate 51 having a suspended membrane 52 formed thereon, a resistive heating element 53 disposed on a surface of the suspended membrane 52, a sorption support structure 54 disposed on the other surface of the suspended membrane 52, and a sorptive material 55 disposed on the sorption support structure 54. The suspended membrane 52 can have an open, flow-through geometry comprising a plurality of holes or annuli formed therein to allow the gas sample to flow through the membrane and reach the sorptive material 55 coated on the sidewalls of the sorption support structure 54. The sorptive material 55 can sorb and concentrate the analytes of interest from the sample gas mixture over time and then can rapidly release the sorbed chemical analytes, upon rapid heating of the sorptive material 55 using the resistive heating element 53, in a concentrated plug for injection into the column 40.

A plurality of through-hole substrates 12 can be aligned, stacked, and bonded together to provide a long GC column 40, similar to a conventional multi-capillary column. Such multi-capillary columns can be used to provide high resolution in a relatively short column by combining many small diameter columns in parallel. Because of the precision lithographic techniques used to fabricate the substrates 12, the parallel array of through holes 11 can have the same diameter and length, and be coated with a uniform thickness of stationary phase material to prevent band broadening and loss of efficiency. Typical hole size can be 3-50 microns in diameter. Since the analyte separation occurs in many small-diameter holes in parallel, fast high resolution separations can be achieved with acceptable sample capacity, resolving power, and pressure drop. For example, a 100×100 array of 4-micron diameter holes in a one-centimeter long column enables a gas flow of about 10 sccm with a pressure drop of about 5 psi. The separated analytes can then be detected with a microfabricated detector 60 at the downstream end of the GC column 40.

The detector 60 can comprise a non-planar thermionic detector (TID), similar to the microfabricated TID disclosed in U.S. patent application Ser. No. 10/981,010 to Lewis et al. A TID, also known as a nitrogen-phosphorous detector, relies on the specific ionization of an analyte near a hot thermionic surface to provide a selective detector. A non-planar microfabricated TID 60 can comprise a microhotplate having a flow-through support structure 62, a resistive heating element 63 disposed on the microhotplate structure 62, a low work function material 64 disposed the surface of the microhotplate structure 62 to provide a thermionic source when heated, and an ion collection electrode 65 disposed in a detection chamber proximate the thermionic source. The electrode 65 collects negative ions generated by the separated analyte reacting with the thermionic source when the microhotplate structure 62 is heated by the resistive heating element 63 and a voltage is applied between the thermionic source and the positively biased electrode. The microfabricated TID can provide high sensitivity and selectivity to nitrogen- and phosphorous-containing compounds and other compounds containing electronegative function groups, enabling the rapid on-site detection of pesticides, chemical warfare agents, explosives, pharmaceuticals, and other organic compounds that contain nitrogen or phosphorus. Other types of specific or non-specific microfabricated detectors can also be integrated with the non-planar microfabricated GC column of the present invention.

The present invention has been described as a non-planar microfabricated gas chromatography column. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A non-planar microfabricated gas chromatography column for separation of analytes in a sample gas mixture, comprising:
   a planar substrate having a plurality of through holes;
   a top lid and a bottom lid bonded to opposite surfaces of the planar substrate, each lid having a plurality of vias to interconnect the plurality of through holes to provide at least one continuous flow channel;
   at least one inlet port in the top or bottom lid for injection of the sample gas mixture; and
   at least one outlet port in the top or bottom lid for elution of the separated analytes.

2. The column of claim 1, where the plurality of vias interconnect the plurality of through holes in a serial column configuration to provide a continuous serpentine flow channel.

3. The column of claim 1, wherein the plurality of vias interconnect the plurality of through holes in a series-parallel column configuration.

4. The column of claim 1, wherein the plurality of vias interconnect the plurality of through holes in a parallel configuration to provide a multi-capillary column.

5. The column of claim 1, further comprising at least one additional planar substrate having a plurality of through holes, wherein the through holes of the at least one additional planar substrate are aligned with the through holes of the planar substrate and the planar substrates are bonded together to provide a multi-layer stack of substrates having longer through holes, and wherein the top lid and the bottom lid are bonded to opposite surfaces of the multi-layer stack.

6. The column of claim 1, wherein the inside surfaces of the plurality of through holes are coated with a stationary phase material.

7. The column of claim 1, wherein the plurality of through holes are packed with a porous packing material.

8. The column of claim 1, wherein the plurality of through holes have a circular cross section.

9. The column of claim 1, wherein the plurality of vias interconnect the plurality of through holes so as to provide at least two separate flow channels.

10. The column of claim 9, wherein the at least two separate flow channels provide a multi-channel chromatography column.

11. The column of claim 9, wherein the at least two separate flow channels provide a multi-dimensional chromatography column.

12. The column of claim 9, wherein the at least two separate flow channels are coated with dissimilar stationary phase materials.

13. The column of claim 1, further comprising a heating element disposed on at least one of the lids.

14. The column of claim 13, wherein the heating element comprises a resistive heating element.

15. The column of claim 1, further comprising a cooling element disposed on at least one of the lids.

16. The column of claim 15, wherein the cooling element comprises a thermoelectric cooler.

17. The column of claim 1, wherein the substrate comprises semiconductor material, quartz, glass, graphite, ceramic, plastic, metal, or alloy.

18. The column of claim 17, wherein the semiconductor material comprises silicon.

19. The column of claim 17, wherein the metal comprises copper or nickel.

* * * * *